United States Patent [19]

Edelson et al.

[11] Patent Number: 4,838,852

[45] Date of Patent: Jun. 13, 1989

[54] ACTIVE SPECIFIC IMMUNE SUPPRESSION

[75] Inventors: Richard L. Edelson, Westport, Conn.; Daniel J. Tripodi, Lebanon, N.J.

[73] Assignee: Therakos, Inc., Westchester, Pa.

[21] Appl. No.: 31,490

[22] Filed: Mar. 27, 1987

[51] Int. Cl.⁴ ............................................. A61M 37/00
[52] U.S. Cl. ........................................................ 604/4
[58] Field of Search ................... 604/4, 5, 6, 20, 28; 128/395

[56] References Cited

U.S. PATENT DOCUMENTS

| | | | |
|---|---|---|---|
| 4,321,918 | 3/1982 | Clark, II | 604/4 |
| 4,321,919 | 3/1982 | Edelson | 604/20 |
| 4,398,906 | 8/1983 | Edelson | 604/6 |
| 4,428,744 | 1/1984 | Edelson | 604/6 |
| 4,464,166 | 8/1984 | Edelson | 604/6 |
| 4,568,328 | 2/1986 | King | 604/6 |
| 4,568,542 | 2/1986 | Kronenberg | 435/240 |
| 4,573,960 | 3/1986 | Goss | 604/6 |
| 4,578,056 | 3/1986 | King et al. | 604/6 |
| 4,613,322 | 9/1986 | Edelson | 604/6 |

OTHER PUBLICATIONS

Hardy et al., World J. Surg. 8, 207–213, 1984.
Roitt et al., *Immunology*, pp. 24.3–24.9, 1986.
Roitt et al., *Immunology*, 1985, pp. 24.3–24.9.
Cohen, I. R., Adv. Intern. Med. (1984), 29: 147–165.
Ben-nun, A. et al., Nature (1981), 292: 60–61.
Holoshitz, J. et al., Science (1983), 219: 56–58.
Cohen, I. R., J. Invest. Derm (1985), 85 (Supp. 1): 34s–38s.
Perez, M. et al., Clin Res. (1986), 34: 774A.
Parrish, J. A. et al., N. Engl. J. Med. (1974), 291: 1207–1211.
Melski, J. W. et al., J. Invest. Derm. (1977), 68: 328–335.
Gilchrest, B. A. et al., Cancer (1976), 38: 683–689.
Honigsmann, H. et al., J. Am. Acad. Derm. (1984) 10: 238–245.

*Primary Examiner*—Stephen C. Pellegrino
*Assistant Examiner*—Sharon Rose
*Attorney, Agent, or Firm*—Richard J. Grochala

[57] ABSTRACT

A method is provided for specifically altering the immune system response of a mammal to a specific antigen. The method comprises the steps of: (a) contacting the mammal's immune system with the specific antigen for a suitable time period so as to artificially stimulate said immune system; (b) withdrawing blood cell containing material, including antigen stimulated blood cells, from the mammal; (c) treating the withdrawn material or cells so as to alter the stimulated cells; and (d) returning the material and treated cells to the mammal.

25 Claims, No Drawings

ACTIVE SPECIFIC IMMUNE SUPPRESSION

BACKGROUND OF THE INVENTION

Throughout this application, various publications are referenced. The disclosures of these publications in their entireties are hereby incorporated by reference into this application in order to more fully describe the state of the art as known to those skilled therein as of the date of the invention described and claimed herein.

This invention relates to methods for specifically altering the immune system response of a mammal wherein specific forms of immune suppression in the mammal are elicited when the mammal is actively immunized in response to a specific antigen.

An immune response may be classified as either a humoral response or a cell-mediated response. A humoral response is one which is mediated by freely diffusible antibody molecules. A cell-mediated response is mediated by specifically reactive lymphocytes, such as T cells, rather than antibodies.

Basic differences exist between humoral and cell-mediated reactions. The time course from exposure to an antigen until the formation of an immune response is minutes to hours for humoral immunity and one or more days for cell-mediated immunity. The active unit which reacts with the antigen is an antibody in humoral immunity and a T lymphocyte in cell-mediated immunity. Humoral antibodies are generally specific for small antigenic determinants. T lymphocytes are specific for larger molecules, usually proteins (in particular, those carried on cell surfaces).

While a cell-mediated response is generally a beneficial part of the body's defenses, certain cell-mediated responses are harmful. Examples of such harmful cell-mediated immune responses include delayed-type hypersensitivity reactions, rejections of allografts, graft-vs.-host reactions and some allergic reactions. Additionally, some autoimmune diseases are also included, such as myasthenia gravis, rheumatoid arthritis, systemic lupus erythematosus and Grave's disease.

Many of these harmful cell-mediated responses involve tissue destruction in a patient and understandably, it would be desirable to eliminate or reduce the effect of such a response. One such response that is of interest is the rejection of allografts. An allograft is a cell, tissue or organ that is transferred from a donor to a genetically different recipient of the same species. Because of extensive polymorphism of certain surface glycoproteins, the grafted cells almost always have on their surfaces histocompatibility or transplantation antigens that are lacking on host cells and vice versa. The resulting host response leads to destruction of the allograft through a cell mediated response.

The graft-vs.-host reaction occurs when lymphocytes are transferred from an immunologically competent donor (normal adult) to an allogeneic incompetent recipient (e.g. newborn). These reactions have increasing clinical importance because of therapeutic attempts to transfer normal thymus or bone marrow cells to immunodeficient humans (e.g., infants with genetic defects, patients with leukemia treated with cytotoxic drugs and whole-body x-irradiation).

In autoimmune disorders, the immune system of the body fails to recognize certain cells or parts of cells as its own and begins attacking those cells with resulting tissue destruction. This attack is effected by the production of autoantibodies and autoreactive T cells.

Allergic responses involve a heightened immune response. In some allergic responses, the immune system mounts an attack against a normally harmless substance, such as pollen, animal dander or dust. In these allergic responses, sensitized T lymphocytes react with the antigen and produce inflammation through the action of lymphokines. Disease results from the deleterious effect of the resulting inflammatory reaction to these environmental antigens. An example of such a reaction is allergic contact dermatitis.

The present invention provides a method for specifically altering the immune response of a patient resulting in the amelioration of a specific immune disorder and thereby the deleterious effects of the disorder.

U.S. Pat. Nos. 4,321,919; 4,398,906; 4,428,744; and 4,464,166 (each in the name of Edelson), the contents of each of which is hereby incorporated by reference in its entirety, describe methods for reducing the functioning lymphocyte population of a human subject. The Edelson methods involve treating the blood of a diseased patient wherein the blood cells have been naturally stimulated as a consequence of the disease state. Specifically, the methods involve treating naturally stimulated human blood cells, such as lymphocytes, with a dissolved photoactivatable drug, such as a psoralen, which is capable of forming photoadducts with DNA in the presence of ultraviolet (U.V.) radiation. The lymphocytes are then treated extracorporeally with U.V. radiation thereby modifying the lymphocytes. Following the extracorporeal irradiation, the treated lymphocytes are returned to the patient. The modified lymphocytes are thought to be cleared from the subject's system by natural processes but at an accelerated pace believed attributable to disruption of membrane integrity, alteration of DNA within the cells, or the like conditions often associated with substantial loss of cellular effectiveness or viability.

The methods described in the Edelson patents have recently been used in human clinical studies in patients afflicted with the erythrodermic (Sezary) form of cutaneous T cell lymphoma (CTCL). The results indicated that the method reduced all T cell populations within the patients, but the normal populations of T cells rebounded within four weeks and suppression of malignant cells was more lasting.

A disadvantage of the methods described by Edelson is that they are not suitable for prophylactic use. For example, the Edelson methods cannot be used to selectively suppress the immune system response of a patient to a specific antigen which is characterisitc of an immune disorder and to which the patient has not yet been exposed.

Studies in rodent systems have shown that the intravenous infusion of syngeneic cells from in vitro expanded auto-reactive clones of T cells can induce experimental autoimmune thyroiditis, encephalomyelitis or arthritis (Cohen, IR. Adv. Intern. Med. (1984) 29: 147–165.) However, if cultured cells from the same T cell clones are lethally damaged or attenuated by treatment with irradiation or mitomycin C to form a vaccine and then infused into syngeneic mice or rats, the recipient animal develops resistance to the induction of the disease by the subsequent infusion of viable auto-reactive T cells (Ben-nun, A. et al., Nature (1981), 292: 60–61; Holoshitz, J. et al., Science (1983), 219: 56–58; and Cohen, I. R., J. Invest. Derm (1985), 85 (Supp. 1):

34s–38s). Thus, it has been demonstrated that cell lines of treated autoimmune effector T cells may be used to vaccinate against the autoimmune disorder.

The rodent experiments described above have the disadvantage of requiring the isolation and growth of T cell lines which are capable of producing autoimmune disease. Such cell lines are not readily available for human diseases and can only be obtained, if at all possible, through time consuming effort. Therefore, the methods described in these rodent experiments are not suitable for treating humans. Furthermore, if such human T cell lines could be obtained, a different cell line specific for each autoimmune diseases treated would have to be prepared.

In further rodent experiments, it has been recently shown that the intravenous infusion of 8-methoxypsoralen (8-MOP) and subsequently U.V. treated lymphocytes into syngeneic MRL mice substantially inhibits the development of their systemic lupus erythematosus-like syndrome and lymphoid hyperplasia which they spontaneously develop (Perez, M. et al., Clin. Res. (1986) 34: 774A).

A pilot study described in Parrish, J. A. et al., N. Engl. J. Med (1974), 291: 1207–1211, indicated that combining oral administration of 8-MOP with ultraviolet-A (UVA) exposure of the skin is efficacious in the management of debilitating psoriasis vulgaris, a hyperproliferative disease of the epidermis. This was subsequenly confirmed in a multi-institutional clinical trial (Melski, J. W. et al. J. Invest. Derm. (1977), 68: 328–335). Subsequently, it was also demonstrated that plaque stage cutaneous T cell lymphoma (CTCL), limited to the skin, also responds to this treatment (Gilchrest B. A., et al. Cancer (1976) 38: 683–689; Honigsmann H., et al. J. Am. Acad. Derm. (1984) 10:238–245).

The prior art describes that lymphocytes may be disabled in diseased patients or may be attenuated to create vaccines. However, such knowledge is not useful in preventing disease in humans. The present invention has the advantage of being suitable for selectively preventing immune disorders in human patients. Furthermore, the present invention relies on the convenient stimulation of the patient's own immune system to produce stimulated lymphocytes rather than using time consuming cell culture techniques. Thus, the present invention provides a convenient method for preventing immune disorders which is suitable for being used for treating any immune disorder.

SUMMARY OF THE INVENTION

The present invention provides a method for specifically altering the immune system response of a mammal to a specific antigen, which comprises the following steps:

(a) contacting the mammal's immune system with the specific antigen for a suitable time period so as to artificially stimulate blood cells;

(b) withdrawing blood cell containing material, including antigen stimulated blood cells, from the mammal;

(c) treating said material or cells so as to alter the antigen stimulated cells; and (d) returning the material and altered cells to the mammal.

As used herein, artificially stimulate refers to human intervention requiring the positive step of contacting the mammal's immune system with the specific antigen of interest. The antigen then stimulates an immune response specific for that antigen. The immune response may be the production of B cell lymphocytes or T cell lymphocytes. Artificial stimulation of the immune system is in contrast with natural stimulation wherein the immune system is stimulated naturally as a consequence of disease.

The blood cell containing material may be blood, lymph fluid, bone marrow, lymphatic organ tissue or any other body fluid or tissue which contains blood cells. In a preferred embodiment the material is blood.

In a preferred embodiment of the present invention, a combination of artificial stimulation of blood cells and subsequent photopheresis of the cells is utilized. The method of photopheresis basically involves combining the cells to be treated with a photoactivatable agent, irradiating the cells with activating radiation and returning the treated cells to the patient's body. The photopheresis may be accomplished by forming the blood, or cells or fluid derived from the blood, into an extracorporeal stream and then flowing the stream through a patient treatment station which comprises a thin chamber substantially transparent to UV radiation. The extracorporeal stream is then irradiated in the treatment system with UV radiation in the presence of a dissolved photoactivatable agent. The photoactivatable agent is one which is capable of being transformed by UV radiation from a biologically inert state to a transiently excited state capable of covalently crosslinking DNA in the cells of the treated blood. The cells containing the crosslinked DNA are thereby lethally damaged or at least functionally inactivated.

DETAILED DESCRIPTION OF THE INVENTION

In the method of the present invention, the antigen to which the immune system response is to be suppressed or modified may be any antigen, including those associated with a disorder, pathological condition or disease state such as autoimmune disease, cancer (e.g., a tumor specific antigen), allergy, infectious disease, rejection of allografts, delayed type hypersensitivity reaction and graft-vs-host reaction. The patient or host to be treated is a mammal, such as a human.

The specific antigen of interest may serve to stimulate a T cell expressing unique T cell receptors which are capable of serving as clonotypic antigens. In such a case, clonal expansion of these circulating aberrant T cells mediates the disorder sought to be controlled. The present invention provides a method for inducing a clone-specific immune reaction which limits the activity of such an aberrant population of T cells.

The contacting of the mammal's immune system with the specific antigen may be achieved in any manner which introduces the antigen into the mammal's immune system, e.g. by injection directly into the blood stream, the lymphatic system or the lymphoid organs. The antigen is then permitted to be in contact with or exposed to the mammal's immune system for a suitable time period so as to permit stimulation of certain blood cells specifically in response to that antigen. This suitable period of time could be as long as one year but in most instances is shorter and generally is no longer than 72 hours.

In a preferred embodiment, the antigen stimulated blood cells, such as stimulated lymphocytes, are withdrawn from the mammal via its blood. This mode is preferred because withdrawal of blood and recirculation to the patient is simple and convenient. Such methods are well known in the art and are analogous to those used in blood dialysis.

Another reason for withdrawing blood to obtain the antigen stimulated blood cells is that the cells affected, such as lymphocytes, are present in the blood in large numbers. However, lymphocytes also circulate through the lymph fluid and tissue spaces and they aggregate in the primary and secondary lymphatic structures, such as the thymus, spleen and lymph nodes. Thus, antigen activated lymphocytes may also be obtained from the lymph fluid or the primary or secondary lymphatic structures. Activated lymphocytes so obtained are treated and returned to the mammal, as described herein.

In accordance with this invention, after having stimulated the blood cells with the specifically selected antigen, the blood cells are withdrawn from the subject and treated so as to alter them, e.g. to lethally damage or at least functionally inactivate them. Such treatment may be accomplished by several means which will occur to one skilled in the art. For example, exposure to exceedingly high or low temperature, high or low pH, high or low pressure, chemicals, toxins or passage through resinous materials may be utilized to affect the inactivating treatment. In some cases, mere handling of the blood cells will accomplish the desired result. Preferably, however, the treatment is effected by the photopheresis method set forth hereinafter.

The photopheresis method of treating the cells involves the extracorporeal irradiation of blood withdrawn from the subject. In this method, the blood, or fluid or cells derived from the blood, is contacted with a photoactivatable agent which is dissolved in the blood either by mixing the agent with the blood subsequent to withdrawing the blood or by administering the agent orally to the patient prior to withdrawing the blood. The photoactivatable agent may be any agent which is capable of cross-linking with DNA. The class of psoralens are examples of such agents. Preferred psoralens are amino-methyl-trimethyl-psoralen (AMT) and 8-methoxy psoralen (8-MOP). Additional agents may be photoactive pyrene and monoclonal antibodies which have been linked to porphyrin molecules.

When a psoralen is utilized in the photopheresis method, it is desirable to have the psoralen present in the blood at a concentration of from about 1 nanogram to about 100 micrograms per milliliter of blood. The withdrawing of the blood, passage of the blood to the treatment station and return of the blood to the patient may be carried out as one continuous operation. It is preferred that the flow rate of the extracorporeal blood stream be in the range of from about 10 to about 75 ml per minute. It is also preferred that the blood be irradiated with photoenergy in the ultraviolet wavelength range (UVA, UVB, UVC) at a radiation dose level of from about 0.1 to about 100 joules/cm$^2$ of blood surface. Preferably, the dose level is from about 5 to about 60 joules/cm$^2$ of blood surface.

The drug 8-methoxypsoralen has been used to treat lymphocytes because it may be transformed from a biologically inert state by low energy ultraviolet A radiation to a transiently excited state capable of covalently cross-linking DNA and other macromolecules. 8-MOP occurs naturally in a variety of plants, including limes, parsley and figs and in its inactive form is non-toxic to humans at pharmacologic doses. However, UVA, which passes through clear glass and some translucent plastics, activates 8-MOP to a form which cross-links sister strands of DNA by forming bifunctional adducts with pyrimidine bases, thereby transforming the molecule into a potent chemotherapeutic agent. Since the half life of the photo-activated 8-MOP is only in the microsecond range, tissues not simultaneously exposed to both the drug and UVA are spared the toxic effects of the active form.

The optimal wavelength range for activation of 8-MOP in T cells is 334–346 nm. The activated cells may be exposed to UV radiation for a period of from about 1 hour to about 6 hours. Within the optimal wavelength range, an approximately 270 minute exposure to UVA is required to provide the average lymphocyte with 2 joules/cm$^2$ of blood surface area.

Since only oral preparations of 8-MOP are available for clinical use, it is necessary to obtain the appropriate concentration of the drug from plasma removed at the time of treatment. For this purpose, plasma may be taken from the patient during the photopheresis procedure two hours following oral administration of about 0.6 mg/kg of body weight of 8-MOP.

The photopheresis method may be carried out in a single apparatus which comprises a continuous centrifuge for separating leucocytes, i.e. white blood cells, from the blood withdrawn from the patient. The centrifuge may be used in an initial discontinuous leukapheresis step, wherein leucocytes are separated from the blood in one or more cycles. This may be accomplished by having the patient recline in a bed and then leukapheresing heparinized blood during 6 cycles through a continuously spinning centrifuge bowl, permitting removal of a total of about 240 ml of leukocyte enriched blood. This blood may then be pooled with about 300 ml of plasma obtained during the same procedure from the patient (removed 2 hours following ingestion of 0.6 mg/kg of 8-MOP) and 200 ml of sterile normal saline, yielding a final hematocrit of approximateley 6.4±1.7% and containing 30–50% of the number of lymphocytes in the patient's blood at the initiation of the leukapheresis. The total volume may then be passed through a disposable sterile irradiation chamber in order to expose it to (UVA) energy. The chamber may be in the form of a six-chambered disposable cassette.

Each chamber of the cassette may be composed of an outer polycarbonate sheath opaque to UVA and an inner UVA-transparent acrylic tube surrounding a fluorescent UVA source. These two walls, between which the blood is pumped, are approximately 1.0 mm apart. Flow in each chamber is from bottom to top, with shunts connecting the top of each chamber to the bottom of the next chamber. Total volume of the cassette is about 190 ml. Incorporated into this UVA exposure system may be an automatically reversible blood pump to permit continuous recycling of the blood through the cassette and temperature sensors to ensure that the blood is not heated above 41° C. Following exposure of blood to UVA, the entire volume is returned to the patient.

Methods and apparatus useful for irradiating blood are described in U.S. Pat. Nos. 4,573,960; 4,568,328; and 4,578,056. Additional descriptions of methods and apparatus for irradiating blood may be found in the following co-pending, commonly assigned patent applications: U.S. Ser. No. 834,292 entitled "Concurrent On-Line Irradiation Treatment Process"; and U.S. Ser. No. 834,258, "Irradiation Chamber for Photoactivation Patient Treatment System."

In a specific embodiment, the present invention provides a method for suppressing the immune response of a mammal to a tissue allograft, wherein the tissue expresses at least one unique antigen which serves to promote an adverse immunological response in the mammal. The unique antigen of interest may be any type of histocompatibility antigen or alloantigen present on the foreign tissue. The method comprises the following steps:

(a) contacting the mammal's immune system with at least one of said antigens for a suitable time period so as to activate certain lymphocytes;

(b) withdrawing blood, including the antigen activated lymphocytes, from the mammal;

(c) treating the withdrawn blood, or blood derived cells, so as to functionally inactivate the antigen activated lymphocytes; and (d) returning the blood and treated lymphocytes to the mammal.

Although the invention has been described in terms of first artificially stimulating the immune system and then treating the blood cells, it may also be possible that the desired results can also be achieved by first treating the blood cells, such as lymphocytes, before actually stimulating the immune system with a specific antigen. It is envisioned that this could be accomplished by withdrawing blood from the patient and treating the blood in a photopheresis apparatus, returning the treated blood to the patient and then contacting the patient's immune system with a specific antigen. It is contemplated that in this manner, the cells would be altered in such a way so as to make them incapable of recognizing and reacting with the antigen.

The present invention is prophylactic in the sense that it may be used to prevent an undesired immune system response in a patient. For example, in a patient who has not yet been exposed to an antigen associated with an immune disorder, the patient's immune system may be artificially stimulated with the antigen and the stimulated immune system cells altered so as to prevent an undesired immune response. A specific example is the stimulation of the patient's immune system with one or more antigens associated with an allograft that the patient will subsequently receive. Using the methods of the present inventon, such an allograft will not be rejected as it otherwise would be.

Although the present invention has been described as having prophylactic uses, it may also be possible that the invention has therapeutic uses as well. For instance, patients who have been previously exposed to an antigen associated with a disorder, i.e. patients exhibiting the disease state associated with the antigen, have been naturally stimulated by the antigen. It is envisioned that these naturally stimulated patients may also be artificially stimulated by the methods of the present invention to achieve a therapeutic result. In such a method, it may be possible to artificially stimulate the patient by the same antigen or a different antigen according to the methods of the present invention in order to alter the immune system response of the patient and achieve a therapeutic effect as to the disorder.

It is envisioned that the present method would have a therapeutic use for patients who already have a disease such as an autoimmune disorder or cancer. For a patient who has cancer, it is contemplated that the method would be used to artificially stimulate the cancer patient's immune system with a tumor specific antigen to which the patient has already been exposed as a natural consequence of the tumor being present in the patient. It is thought that while the patient's immune system has not attacked the tumor prior to treatment by artificial stimulation, the method of the present invention may alter the immune response of the patient so as to induce an immunological attack on the tumor which previously was not attacked.

While the invention has been described in detail herein, the mechanism by which the immune system is altered is not entirely understood. The alteration of the immune system by the method of the present invention may result in either suppression or activation of the immune system. The immune system may be suppressed so as to ameliorate the immune response to a specific antigen, such as in the allograft example described above. However, it is also contemplated that the immune system may be activated rather than suppressed, such as in the hypothetical tumor example described above.

The following examples were designed to show that the photodestruction of large numbers of T cells belonging to an expanded clone and their introduction into an immune system which has not been directly inhibited by photoactivated 8-MOP may lead to a specific immunological reaction against them. These examples are predicated on the idea that reinfusion of functionally inactivated, intact lymphocytes expressing cell surface antigens may serve to promote an immunologic response in the recipient.

In one model, the delayed hypersensitivity response to a T cell dependent antigen, sheep red blood cells (SRBC), is inhibited by prior tolerance induction using effector cells inactivated with 8-MOP-UVA. In another model, the alloreactive response to foreign histocompatability antigens is inhibited in a murine skin allograft system. In a further model, the murine analog of systemic lupus erythematosus (SLE) developed in the MRL/lpr mouse is ameliorated.

The following examples are presented to illustrate the subject invention. The invention is not to be considered limited by the examples, but only by the appended claims.

EXAMPLE 1

Delayed Hypersensitivity Response to Sheep Red Blood Cells

This example utilized syngeneic mice, i.e. genetically identical members of the same species. Because each mouse is genetically identical, the manipulations and transfer of tissue from one mouse to the another should be viewed as taking place in one individual mouse rather than several different mice. The method of the present invention was utilized to specifically alter the immune system response of the mouse to a specific antigen, namely sheep red blood cells (SRBC). The sheep red blood cells were injected intravenously into BALB/c mice in low amounts ($10^6$). This contacting of the mouse's immune system with the SRBC artificially stimulated its immune system to induce T cell immunity demonstrable as a delayed type hypersensitivity reaction (DTH), but did not induce humoral responses. After a suitable time period, the mice were sacrificed, their spleens removed and the spleen cells were altered by treatment with 8-MOP-UVA. These altered spleen cells were then used to treat naive, syngeneic mice. The details of this procedure are described as follows.

BALB/c mice aged 6–8 wks were divided into two groups and treated weekly by intravenous infusions of:
(1) 8-MOP-UVA inactivated splenocytes from syngeneic mice that had been immunized, i.e. artificially stimulated, 7 days before with $10^6$ SRBC/0.2 ml saline, (Group A) or
(2) Naive splenocytes as a control, (Group B).

For induction of DTH to SRBC, the mice were primed (Pr) with $10^6$ SRBC two days after the sixth treatment. Each mouse received $15 \times 10^7$ inactivated cells. Seven days later, they were challenged (Ch) with $10^8$ SRBC in 50 microliters saline in the subcutaneous tissue of the left hind footpad. The right hind footpad, as a control received 50 microliters saline.

In parallel, additional untreated naive mice were either primed and challenged (Group C) or challenged only (Group D). DTH was measured 24 hr after the elicitation with a dial gauge caliper (Manostat type 6921) calibrated to ±0.05 mm. The level of DTH was expressed as footpad thickness increase in $10^{-2}$ mm between left and right footpads. The data is set forth in Table 1 as geometric means 35 SEM from 4 to 10 mice in each group.

As shown in Table 1, mice in group A were not able to mount a response to SRBC. Group A's DTH response was similar to that observed in negative controls (Group D) which were not treated but challenged with SRBC. In contrast, Group B mice treated with inactivated naive splenocytes exhibited a normal DTH reaction similar to the response observed in the positive control group (Group C).

TABLE 1

| | Delayed type hypersensitivity response to sheep red blood cells | | |
|---|---|---|---|
| Group | Tx (8MOP-UVA inactivated splenocytes) | SRBC Pr/Ch | 24 hr footpad increase ($\times 10^{-2}$ mm) |
| A | SRBC Primed | +/+ | 7 + 1.1 |
| B | Naive | +/+ | 24.8 ± 1.3 |
| C | 0 | +/+ | 19 ± 1.6 |
| D | 0 | −/+ | 6 ± 1.2 |

To test the specificity of this suppression, mice were exposed to a non-related antigen, namely chicken red blood cells (CRBC), after 2 more in vitro treatments. All groups of mice (including those which had been tolerized to SRBC) exhibited a normal level of DTH to CRBC. This demonstrates that the suppression was specific for the lymphocytes activated by the SRBC antigen.

To further elucidate the cellular mechanism of unresponsiveness to SRBC, passive cell transfer into normal recipients was performed immediately after the DTH reaction to SRBC. 24 hours after the DTH reaction, spleens were removed from each group of mice. Groups A & B were treated with inactivated SRBC primed splenocytes or inactivated naive cells. The non-treated groups were primed and challenged (Group C) or challenged only (Group D). $45 \times 10^6$ cells from each group were intravenously injected into naive recepients. Immediately after the transfer, mice were challenged in the footpad and DTH was measured 24 hours later. The results are set forth in Table 2. Recipients which received cells from SRBC tolerized animals (Group A), in contrast to the other groups, did not develop a DTH reaction.

TABLE 2

| | Transfer of tolerance to sheep red blood cells | | | |
|---|---|---|---|---|
| Group | Cell Source Tx w/8MOP-UVA cells IV | SRBC Pr/Ch | Post-transfer SRBC Challenge | 24 hr footpad increase ($\times 10^{-2}$ mm) |
| A | SRBC Primed | +/+ | + | 3.9 ± 1.8 |
| B | Naive | +/+ | + | 15.7 ± 1.9 |
| C | 0 | +/+ | + | 15 ± 3.2 |
| D | 0 | −/+ | + | 4.5 ± 1.4 |

These results demonstrate that repeated infusion of 8MOP-UVA inactivated antigen primed cells into normal recipients induces suppression of the T cell immunity, as measured by the DTH reaction, rendering these mice tolerant to that antigen. This tolerance may be due to either the lack of sufficient effector cells or the presence, or stimulation of endogenous suppressor cells.

These murine models validate the concept that T cell mediated immune responses may be immunoregulated by first artificially stimulating the immune system and then exposing the immune system to effector cells inactivated with 8MOP-UVA. The power of this approach for therapy of autoimmune disease is demonstrated in Example 3 wherein the manifestations of fulminant autoimmune disease were controlled in the MRL/lpr mouse model.

EXAMPLE 2

Induction of Allograft Tolerance

Tolerance to skin allografts i.e. a tissue graft between two genetically dissimilar members of the same species, was studied in an allogeneic system. In this system, BALB/c mice received histoincompatible grafts, i.e. having incompatible transplantation antigens, from CBA/J donors. Mice receiving histoincompatible grafts will normally reject the graft. When graft rejection ensued, the mice were sacrificed and their spleen cells inactivated with 8MOP and UVA. These inactivated splenocytes were injected into naive BALB/c recipients. After 8 treatments of inactivated syngeneic splenocytes from mice undergoing transplant rejection, the BALB/c recipients were challenged with an alloantigen present on the CBA/J allograft resulting in a delayed type hypersensitivity reaction.

The methodology utilized is as follows: BALB/c mice were tolerized to CBA/J alloantigens by 8 injections of splenocytes from syngeneic BALB/c mice that were rejecting CBA/J allografts. The tolerized BALB/c mice were primed with $30 \times 10^6$ 8MOP-UVA inactivated splenocytes from a BALB/c mouse. The tolerized mice were challenged in the dorsum of the foot with $10 \times 10^6$ $H_2^k$ splenocytes. Tolerized mice were challenged with a second alloantigen ($H_2^b$). Naive BALB/c mice were primed and challenged to both alloantigens. Negative controls were naive BALB/c mice that received no priming dose but were challenged with alloantigens. The results are set forth in Table 3. $H_2$ refers to a region of the mouse Major Histocompatibility Complex (MHC) genome which produces products important in the rejection process. The $H_2$ complex is furthered subdivided into regions, one of which is the D-region. The D-region contains genes encoding proteins which act as cell surface recognition molecules.

TABLE 3

Delayed hypersensitivity response of Balb/C ($H_2^d$) mice tolerized to CBA/J ($H_2^k$) alloantigens

| BALB/c N = 5 | $H_2$ | Primed | Chall. | DTH (mm × $10^{-2}$) (X ± SD) | % Suppr. |
|---|---|---|---|---|---|
| Naive Pos. Control | D | $H_2^k$ | $H_2^k$ | 84.4 ± 13 | |
| Naive Neg. Control | D | — | $H_2^k$ | 8.9 ± 3.7 | |
| Tol. to $H_2^k$ | D | $H_2^k$ | $H_2^k$ | 19.9 ± 6.0 | 85.5 |
| Naive Pos. Control | D | $H_2^b$ | $H_2^b$ | 73.4 ± 15.4 | |
| Naive Neg. Control | D | — | $H_2^b$ | 18.0 ± 4.0 | |
| Tol. to $H_2^k$ | D | $H_2^b$ | $H_2^b$ | 74.3 ± 2.5 | 0.0 |

The tolerized mice demonstrated 86% suppression of the delayed hypersensitivity response to CBA/J alloantigens. This suppression was specific for products of the $H_2^k$ locus, since tolerized BALB/c mice challenged with $H_2^b$ splenocytes were capable of responding to this alloantigen to the same extent as naive BALB/c mice. Therefore, specific tolerance to alloantigens may be induced by repeated injections of cells from the spleens of mice that are undergoing a graft rejection response.

The spleens of mice rejecting an allograft contain effector cells that are specifically reactive for foreign histocompatibility antigens. Repeated transfers of these syngeneic effector cells inactivated with 8MOP-UVA into BALB/c mice may cause a response in the recipient mouse which suppresses the effector cell population. When these mice are challenged with the relevant alloantigen they cannot mount an effector cell response since they have suppressed the responding cell population. This observation is supported by the results of a cytotoxicity assay.

T cell mediated immunity may be demonstrated in an in vitro cytotoxicity assay, such as release of $^{51}Cr$ from a pre-labelled target cell. In such an assay, cytotoxic T cell effector function is monitored by incubating lymphocyte effector cells with the radiolabelled target cells. The lytic action of the effectors is meaured by assaying released isotope. In such a cytotoxicity assay, BALB/c splenocytes were obtained from mice that were tolerized to CBA/J alloantigens by injecton of 8-MOP-UVA inactivated splenocytes from BALB/c mice that were rejecting a CBA/J allograft. Effector cells were cultured at $8 \times 10^6$/cc with $3 \times 10^6$/cc CBA/J splenocytes inactivated with 8MOP-UVA as stimulator cells for 7 days. Target cells were CBA/J concanavalin A blasts (T cell lymphocytes stimulated by the mitogenic lectin Con A) that were labeled with $^{51}Cr$ and added at appropriate effector to target ratios. The targets were incubated for 4 hours and the effector cells and supernatants were harvested for liquid scintillation counting. The results of this assay are set forth in Table 4.

TABLE 4

Cytotoxicity Assay: BALB/c tolerized to CBA/J alloantigens

| Effector | Stimulator | Target | % Lysis Effector to Target Ratio | | |
|---|---|---|---|---|---|
| | | | 20:1 | 40:1 | 80:1 |
| BALB/c Naive | CBA/J | CBA/J | 31 ± 7.8 | 62.1 ± 19.2 | 53.5 ± 17.2 |
| BALB/c transpl- w/CBA/J allograft | None | CBA/J | 73.3 ± 7.1 | ND | 81.2 ± 0 |
| BALB/c transpl- w/CBA/J allograft | CBA/J | CBA/J | 75.9 ± 4.4 | 42.5 ± 2 | 52 ± 16.8 |
| BALB/c tolerized to CBA/J | CBA/J | CBA/J | 20.4 ± 3.9 | 19.2 ± 3.7 | 26.9 ± 6.6 |

As can be seen from Table 4, naive BALB/c mice and BALB/c mice sensitized to CBA/J skin grafts effectively lysed CBA/J targets at all effector to target ratios studied. Splenocytes from BALB/c mice that were tolerized by injection of effector cell populations from spleens of mice rejecting CBA/J grafts exhibited 48% to 67% suppression of the capacity to generate cytotoxic T cells capable of lysing CBA/J targets.

The inactivated splenocytes also suppressed the cytotoxic response of naive and sensitized BALB/c splenocytes when they were added as third party cells to a standard cytotoxicity assay. Therefore, the spleens of tolerized mice contained cells that did not respond to the relevant alloantigen and that were capable of suppressing an effector cell response in vitro. These results support the proposition that reinfusion of 8-MOP-UVA inactivated effector cell populations promotes a host response which down-regulates the immunoreactive cell type. This immuno-suppressive response is antigen specific.

EXAMPLE 3

Treatment of Murine Autoimmune Disease

The MRL/lpr model of systemic lupus erythematosus (SLE) is a model wherein the MRL/lpr strain of mice develop an autoimmune disease similar to human SLE. In this example, young mice (4–6 wk of age) were treated, prior to the onset of autoimmune disease, with 8MOP-UVA inactivated syngeneic splenocytes from old autoimmune mice (18–22 wk). The manifestations of autoimmune disease in the MRL/lpr mouse include massive T cell hyperproliferation leading to lymph node hyperplasia of spleen and lymph nodes.

The T cell proliferation consists of lymphoid cells that are THY1+, LY1+, T cells. Therapy that abolishes this T cell proliferation has been shown to inhibit the development of autoimmune disease in MRL/lpr mice. Therefore, it was postulated that if young mice are treated prior to the onset of autoimmune disease, an autoregulatory immune response would be induced which would ameliorate the fulminant course of their autoimmune disease. The present results confirmed this postulate.

The MRL/lpr mice have a number of consistent disease features that provide reliable indicators of the efficacy of the treatment protocol. The following parameters of autoimmune disease were followed in age-matched MRL/lpr mice:

1. Spleen and lymph node weight, size and cellularity;

2. Survival;
3. Anti-DNA autoantibody titers;
4. Lymphocyte phenotype; and
5. Response to T and B cell mitogens.

8MOP-UVA treated MRL/lpr mice received biweekly intravenous injections in the tail vein of $20-50\times10^6$ splenocytes treated with 100 ng/ml 8MOP and 1 joule/cm$^2$ UVA. Control mice received no treatment. Mice were sacrificed at weekly intervals and comparisons of spleen and lymph node size, weight, and cellularity were performed. The results of sequential autopsies on age-matched 8MOP-UVA treated and untreated control MRL/lpr mice are presented in Table 5.

TABLE 5

Comparison of spleens and lymph nodes from 8MOP-UVA treated MRL/1 pr mice and age-matched controls

| Group | Age (wk) | N | Spleen Wt (g) | Spleen cell yield ($\times 10^6$) | Size (cm$^2$) |
|---|---|---|---|---|---|
| 8MOP- | 13–19 | 5 | 0.31 ± 0.07 | 229 ± 115 | 1.11 ± 0.32 |
| UVA | 20–26 | 7 | 0.29 ± 0.16 | 71 ± 0.52 | 1.26 ± 0.45 |
|  | 29–32 | 3 | 0.98 ± 0.56 | 500 ± 80 | 3.0 ± 0.53 |
| No Tx | 13–19 | 19 | 0.53 ± 0.23 | 323 ± 90 | 1.77 ± 0.77 |
|  | 20–26 | 20 | 0.63 ± 0.22 | 364 ± 167 | 1.92 ± 0.80 |
|  | 29–32 | Age-matched controls - 100% mortality | | | |

(Part II)

| Group | Age (wk) | Lymph Node Wt (g) | Size (cm$^2$) |
|---|---|---|---|
| 8MOP- | 13–19 | 0.48 ± 0.33 | 1.28 ± 0.79 |
| UVA | 20–26 | 0.62 ± 0.39 | 1.44 ± 0.60 |
|  | 29–32 | 1.00 ± 0.77 | 1.70 ± 1.20 |
| No Tx | 13–19 | 0.87 ± 0.43 | 2.14 ± 1.5 |
|  | 20–26 | 1.38 ± 0.64 | 2.35 ± 1.26 |
|  | 20–32 | 100% Mortality | |

The MRL/lpr mice treated with syngeneic 8MOP-UVA splenocytes from autoimmune donors show a decrease in spleen and lymph node weight, size and cellularity in comparison with age-matched, control, untreated mice at 13–19 wk. The spleens of treateed mice weighed 49% less and had 29% fewer splenocytes than control mice. Lymph nodes from 8MOP-UVA treated mice at 13–19 wks were 45% smaller in weight and 40% smaller in size than controls. This decrease was even more marked in the group of 8MOP-UVA treated mice sacrificed at 20–26 wks. A 54% decrease (P<0.001) in splenocyte yield was evident in the 8MOP-UVA treated group. Similarly, the lymph nodes obtained from the 8MOP-UVA treated mice at 20–26 wks weighed 55% (P<0.01) less and were 39% smaller in size than controls.

A group of 8MOP-UVA treated mice were allowed to survive past the age when all untreated control mice had died (22–26 wks.) These mice were sacrificed at 29–32 wks of age, an increase in life span of more than two months. Organomegaly was present in these very old mice suggesting that the reinfusion of 8MOP-UVA treated autoimmune splenocytes delays the onset of MRL/lpr autoimmune disease, but that eventually lymphoid hyperplasia will occur.

In another study, MRL/lpr mice treated with 8MOP-UVA splenocytes were tested for production of anti-DNA autoantibodies. Sera were obtained by bleeding mice from the retro-orbital plexus. Calf thymus DNA was sonicated and dried onto microtiter wells at 10 mg/well. The sera were added to the wells and the plates rotated for 1 hr at 23° C. After washing, reactive antibodies were detected by the binding of an $^{125}$I labeled rabbit anti-mouse Ig reagent. The results of this study are set forth in Table 6.

TABLE 6

Anti-DNA antibody titers in MRL/1 pr mice treated with 8MOP-UVA

| Group | Age/Wk | Anti-DNA anti-body titer 1:100 CPM |
|---|---|---|
| MRL/1 pr | 13 | 901 ± 858 |
| TX 8MOP-UVA | 19 | 1,971 ± 772 |
| MRL/1 pr | 13 | 6,355 ± 733 |
| no Tx | 17 | 15,063 ± 4,482 |
| Normal mice |  | 2,353 ± 670 |
| BALB/c |  | 2,353 ± 120 |
| CBA/J |  |  |

The MRL/lpr mice treated with 8MOP-UVA inactivated autoimmune splenocytes did not develop high titers of anti-DNA antibodies. At 19 wks. of age, sera from 8MOP-UVA treated mice contained background levels of anti-DNA antibodies similar to those obtained in normal non-autoimmune mice. Untreated MRL/lpr mice had high levels of anti-DNA antibodies detectd at 13 wks. of age and these levels rose to 6× normal by 17 wks. of age. Therefore, reinfusion of 8MOP-UVA treated syngeneic autoimmune splenocytes inhibits the induction of anti-DNA autoantibodies which is consistent with an attenuation of the disease.

In phenotypic studies of lymphocytes from spleens of 8MOP-UVA treated mice, a 65% decrease in THY1+ T cells was detected in comparison with untreated controls. The LY1+ population declined by 50%. A 2-fold increase in surface immunoglobulin positive B cells was evident in the spleens of treated mice. If these B cells were lysed, a 6-fold increase in an Ia+ cell-type was detected. Preliminary functional studies have already shown that splenocytes from 8MOP-UVA treated mice retain the capacity to respond to the T cell mitogen concanavalin A and the B cell mitogen lipopolysaccharide while splenocytes from untreated mice lose the capacity to respond to both T and B cell mitogens.

Taken as a whole, these results demonstrate that the course of autoimmune disease in MRL/lpr mice may be ameliorated by exposure at a young age to 8MOP-UVA inactivated splenocytes. The fulminant lymphoid hyperplasia is delayed in onset and treated mice survive at least two months longer than untreated littermates. In addition, the production of anti-DNA autoantibodies is inhibited in treated mice. The spleens of treated mice contain fewer T cells and increased percentages of B cells and Ia+ cells. Also treated mice retain the capacity to mount a proliferative response to T and B cell mitogens. By artificially stimulating the animal's immune system prior to the initiation of the disease, the method described herein altered the course of the disease.

While the present invention has been particularly described in terms of specific embodiments thereof, it will be understood in view of the present disclosure, that numerous variations upon the invention are now enabled to those skilled in the art, which variations yet reside within the scope of the present invention. Accordingly, the invention is to be broadly construed and limited only by the scope and spirit of the claims now appended hereto.

What is claimed is:

1. A method for altering the immune system response of a patient to a specific antigen, comprising:

(a) artificially introducing the specific antigen into the patient's bloodstream or immune system by injection so as to artificially stimulate said immune system;

(b) withdrawing blood cell containing material, including antigen stimulated blood cells, from the patient;

(c) treating said material or cells with UV radiation in the presence of a photoactivatable agent; and (d) returning the treated material or cells to the patient.

2. The method of claim 1, wherein the treating of step (c) comprises mixing the photoactivatable agent with the withdrawn material and irradiating the mixture with UV radiation.

3. The method of claim 1, wherein the photoactivatable agent is administered to the patient prior to step (b).

4. The method of claim 1, wherein the treating comprises the steps of:

forming said material into an extracorporeal stream, flowing said stream through a treatment chamber substantially transparent to UV radiation and irradiating the stream in the chamber with UV radiation in the presence of the photoactivatable agent.

5. The method of claim 1, wherein the blood cell containing material is blood, lymph fluid, bone marrow or lymphatic organ tissue.

6. The method of claim 1, wherein the antigen is associated with a disorder selected from the group consisting of delayed-type hypersensitivity reaction, autoimmune disease, cancer, allergy, infectious disease, rejection of allografts and graft vs. host reaction.

7. The method of claim 1, wherein the mammal is a human.

8. The method of claim 1, wherein the cells are lymphocytes.

9. The method of claim 8, wherein the lymphocytes are T cells.

10. The method of claim 1, wherein the antigen is a T cell expressing unique T cell receptors which are capable of serving as clonotypic antigens.

11. The method of claim 6, wherein the disorder is mediated by the clonal expansion of circulating aberrant T cells.

12. The method of claim 1, wherein the photoactivatable agent is a psoralen.

13. The method of claim 12, wherein the psoralen is 8-methoxy psoralen or amino-methyl-trimethyl psoralen.

14. The method of claim 12, wherein the psoralen is present in the blood at a concentration from about 1 nanogram to about 100 micrograms per milliliter of blood.

15. The method of claim 4, wherein the withdrawing of the material, passage to the treatment station, and return of the material to the patient is carried out as a continuous operation.

16. The method of claim 15, wherein the flow rate of the extracorporeal stream is in the range of from about 10 to about 75 ml/min.

17. The method of claim 15, which further comprises separating at least portions of the cells before returning the cells to the patient, by passing the stream through a continuous flow centrifuge.

18. The method of claim 1, wherein the material is irradiated with photoenergy in the UVA wavelength and at a radiation dose level of from about 0.1 to about 100 joules/cm$^2$.

19. The method of claim 1, wherein the stimulation comprises the formation of certain lymphocytes specifically in response to the antigen.

20. The method of claim 1, wherein the membrane integrity of the stimulated cells is disrupted in step (c).

21. The method of claim 1, wherein the DNA within the stimulated cells is altered in step (c).

22. A method for suppressing the immune system response of a patient to a tissue allograft prior to receipt of the allograft, wherein the tissue expresses at least one unique antigen which serves to promote an adverse immunologic response in the patient, comprising:

(a) artificially introducing at least one of said antigens into the patient's bloodstream or immune system by injection so as to activate certain lymphocytes which are specifically reactive with said antigen;

(b) withdrawing blood cell containing material, including the antigen activated lymphocytes, from the patient;

(c) treating said lymphocytes with UV radiation in the presence of a photoactivatable agent; and (d) returning the treated lymphocytes to the patient.

23. A method for altering the immune system response of a patient to a specific antigen, comprising:

(a) administering the specific antigen to the patient by injection so as to artificially stimulate the patient's immune system;

(b) administering a photoactivatable agent to the patient;

(c) withdrawing blood cell containing material, including antigen stimulated blood cells, from the patient;

(d) treating said material or cells with UV radiation; and (e) returning the treated material or cells to the patient.

24. The method of claim 23, wherein the antigen is an antigen to which the patient has not been previously exposed.

25. The method of claim 23, wherein the administering of step (b) is oral.

* * * * *

UNITED STATES PATENT AND TRADEMARK OFFICE
CERTIFICATE OF CORRECTION

PATENT NO. : 4,838,852

DATED : June 13, 1989

INVENTOR(S) : Richard L. Edelson, Daniel J. Tripodi

It is certified that error appears in the above-identified patent and that said Letters Patent is hereby corrected as shown below:

Claim 7, column 15, line 33:  "mammal" should read --patient--.

Claim 15, column 15, line 55:  "station" should read --chamber--.

Signed and Sealed this

Sixth Day of March, 1990

Attest:

JEFFREY M. SAMUELS

Attesting Officer

Acting Commissioner of Patents and Trademarks